(12) United States Patent
Offidani

(10) Patent No.: US 12,019,980 B2
(45) Date of Patent: Jun. 25, 2024

(54) APPARATUS, SYSTEM, AND METHOD FOR ADAPTIVE PARSING AND PROCESSING OF TEXT TO FACILITATE USER ENGAGEMENT

(71) Applicant: Click Therapeutics, Inc., New York, NY (US)

(72) Inventor: Emanuela Offidani, New York, NY (US)

(73) Assignee: CLICK THERAPEUTICS, INC., New York, NY (US)

( * ) Notice: Subject to any disclaimer, the term of this patent is extended or adjusted under 35 U.S.C. 154(b) by 490 days.

(21) Appl. No.: 17/286,000

(22) PCT Filed: Nov. 19, 2020

(86) PCT No.: PCT/US2020/061357
§ 371 (c)(1),
(2) Date: Apr. 16, 2021

(87) PCT Pub. No.: WO2021/102183
PCT Pub. Date: May 27, 2021

(65) Prior Publication Data
US 2022/0366132 A1   Nov. 17, 2022

Related U.S. Application Data

(60) Provisional application No. 62/397,510, filed on Nov. 19, 2019.

(51) Int. Cl.
*G06F 40/205* (2020.01)
*G06F 40/30* (2020.01)
(Continued)

(52) U.S. Cl.
CPC ............ *G06F 40/205* (2020.01); *G06F 40/30* (2020.01); *G16H 10/20* (2018.01); *G16H 20/10* (2018.01)

(58) Field of Classification Search
CPC ....... G06F 40/205; G06F 40/30; G16H 20/10; G16H 10/20
See application file for complete search history.

(56) References Cited

U.S. PATENT DOCUMENTS

| 2010/0169352 A1* | 7/2010 | Flowers | G06F 16/951 |
| | | | 707/E17.071 |
| 2014/0074454 A1* | 3/2014 | Brown | G10L 15/08 |
| | | | 704/235 |

(Continued)

FOREIGN PATENT DOCUMENTS

KR    101785780 B1    10/2017

OTHER PUBLICATIONS

International Search Report, International Searching Authority, Korean Intellectual Property Office, Mar. 19, 2021.

(Continued)

*Primary Examiner* — Fan S Tsang
*Assistant Examiner* — David Siegel
(74) *Attorney, Agent, or Firm* — Bochner PLLC; Andrew D. Bochner

(57) ABSTRACT

A computer system for adaptive parsing and processing of text to facilitate user engagement in a remote computing environment on an electronic device comprising one or more processors, one or more computer-readable memories, and one or more computer-readable storage devices, and program instructions stored on at least one of the one or more storage devices for execution by at least one of the one or more processors via at least one of the one or more memories is provided. The stored program instructions include receiving an input content from the electronic device of a user, the input content comprising a plurality of words, the plurality of words comprising one or more content words and one or more function words; following the receiving of the input content, extracting the function words and the (Continued)

content words from the input content; following the extracting of the input content, analyzing the function words and the content words extracted from the input content; determining, based on the extraction of the input content including the function words and the content words, user information; determining, based on the user information, output content to output to the user; and outputting, to a screen of the electronic device of the user, the output content.

9 Claims, 26 Drawing Sheets

(51) Int. Cl.
    *G16H 10/20*     (2018.01)
    *G16H 20/10*     (2018.01)

(56) References Cited

U.S. PATENT DOCUMENTS

| | | |
|---|---|---|
| 2017/0206328 A1 | 7/2017 | Mizoguchi et al. |
| 2017/0221472 A1* | 8/2017 | Sharifi .................. G10L 13/08 |
| 2018/0121603 A1 | 5/2018 | Devarakonda et al. |
| 2019/0311814 A1 | 10/2019 | Kannan et al. |

OTHER PUBLICATIONS

Written Opinion of the International Searching Authority, International Searching Authority, Korean Intellectual Property Office, Mar. 19, 2021.

\* cited by examiner

```
//TextRecognitionController.py
try:
    from PIL import Image
except ImportError:
    import Image
import pytesseract
import nltk
from nltk import tokenize, CFG
import codecs
from spellchecker import SpellChecker
import language_check
import re
from nltk.tree import * class TextRecognitionController:
    image = ''
    recognized = ''
    sentences = []
    words = []
    pos_tags = []

pos_tags_map = {
        'CC': 0, 'CD': 0, 'DT': 0, 'EX': 0, 'FW': 0, 'IN': 0, 'JJ': 0,
        'JJR': 0, 'JJS': 0, 'LS': 0, 'MD': 0, 'NN': 0, 'NNS': 0, 'NNP': 0,
        'NNPS': 0, 'PDT': 0, 'POS': 0, 'PRP': 0, 'PRP$': 0, 'RB': 0, 'RBR': 0,
        'RBS': 0, 'RP': 0, 'TO': 0, 'UH': 0, 'VB': 0, 'VBD': 0, 'VBG': 0,
        'VBN': 0, 'VBP': 0, 'VBZ': 0, 'WDT': 0, 'WP': 0, 'WP$': 0, 'WRB': 0,
```

*FIG. 3A*

```
} functional_words = {
    'prepositions': [],  # IN
    'pronouns': [],  # PRP, PRP$, WP, WP$
    'determiners': [],  # DT, WDT
    'conjunctions': [],  # CC
    'auxiliaries': [],  # VBZ, VBP
    'particles': []  # UH
} content_words = {
    'nouns': [],  # NN, NNS, NNP, NNPS
    'adjectives': [],  # JJ, JJR, JJS
    'verbs': [],  # VB, VBD, VBG, VBN, VBP, VBZ
    'adverbs': [],  # RB, RBR, RBS
} phrase_structures = {
    'conjunctions': [],
    'dependent_clauses': [],
    'prepositions': [],
    'determiners': [],
    'particles': []
} sentences_factors = []
```

*FIG. 3B*

```
text_sent_count = 0 text_map = {
    'pos_tags_map': pos_tags_map,
    'content_words': content_words,
    'phrase_structures': phrase_structures,
    'sentences_factors': sentences_factors,
    'functional_words': functional_words,
    'text_sent_count': text_sent_count,
} def __init__(self, image):
    self.image = image def recognize(self, case):
    image = Image.open('tests/' + case + '/' + self.image)
    print(pytesseract.image_to_string(image))
    text = pytesseract.image_to_string(image)
    self.recognized = text
    return self.recognized def get_sentences(self):
    self.sentences = tokenize.sent_tokenize(self.recognized)
    print(self.sentences)
    return self.sentences def get_words(self):
    self.words = tokenize.word_tokenize(self.recognized)
```

*FIG. 3C*

```
    print(self.words)
    return self.words def get_pos_tags(self):
    self.pos_tags = nltk.pos_tag(self.words)
    print(self.pos_tags)
    return self.pos_tags def build_word_pos_tags_map(self):
    for tag in self.pos_tags:
        try:
            self.pos_tags_map[tag[1]] += 1
        except:
            continue self.text_sent_count = len(self.sentences)

self.set_content_words()
    self.set_functional_words()
    self.set_sentences_factors()

print(self.text_map)

def set_content_words(self):
    for tag in self.pos_tags:
        try:
```

*FIG. 3D*

```
        if tag[1] in ['NN', 'NNS', 'NNP', 'NNPS']:
            self.content_words['nouns'].append(tag[0])
        if tag[1] in ['JJ', 'JJR', 'JJS']:
            self.content_words['adjectives'].append(tag[0])
        if tag[1] in ['VB', 'VBD', 'VBG', 'VBN', 'VBP', 'VBZ']:
            self.content_words['verbs'].append(tag[0])
        if tag[1] in ['RB', 'RBR', 'RBS']:
            self.content_words['adverbs'].append(tag[0])
      except:
        continue def set_functional_words(self):
    for tag in self.pos_tags:
      try:
        if tag[1] in ['IN']:
            self.functional_words['prepositions'].append(tag[0])
        if tag[1] in ['PRP', 'PRP$', 'WP', 'WP$']:
            self.functional_words['pronouns'].append(tag[0])
        if tag[1] in ['DT', 'WDT']:
            self.functional_words['determiners'].append(tag[0])
        if tag[1] in ['CC']:
            self.functional_words['conjunctions'].append(tag[0])
        if tag[1] in ['VBZ', 'VBP']:
            self.functional_words['auxiliaries'].append(tag[0])
        if tag[1] in ['UH']:
            self.functional_words['particles'].append(tag[0])
      except:
        continue
```

*FIG. 3E*

```python
def set_sentences_factors(self):
    for sentence in self.sentences:
        sentence = {
            'sentence_text': sentence,
            'sentence_length': len(sentence),
            'sentence_complexity': self.check_sentence_complexity(sentence),
            'grammar_compliance': self.check_grammar_compliance(sentence),
            'spelling_compliance': self.check_spelling_compliance(sentence),
            # 'vocabulary_level': 0
        }
        self.sentences_factors.append(sentence)

def check_grammar_compliance(self, sentence=''):
    tool = language_check.LanguageTool('en-US')
    matches = tool.check(sentence)
    return len(matches)

def check_spelling_compliance(self, sentence=''):
    spell = SpellChecker()
    sentence_words = tokenize.word_tokenize(sentence)
    misspelled = spell.unknown(sentence_words)
    i = 0
    for word in misspelled:
        if word is spell.correction(word):
            i += 1
    return i
```

*FIG. 3F*

```python
    def get_text_map(self):
        for k, v in self.pos_tags_map.items():
            print(k, v)
        print(self.text_sent_count)
        print(self.functional_words)
        print(self.content_words)
        print(self.text_map)
        return self.text_map def check_sentence_complexity(self, sentence=''):
        self.check_phrase_structures(sentence)
        sum = len(self.phrase_structures['conjunctions'])
        sum += len(self.phrase_structures['dependent_clauses'])
        sum += len(self.phrase_structures['prepositions'])
        sum += len(self.phrase_structures['determiners'])
        sum += len(self.phrase_structures['particles'])
        return sum def check_phrase_structures(self, sentence=''):
        tagged_sentence = nltk.word_tokenize(sentence)
        tagged_sentence = nltk.pos_tag(tagged_sentence)
        dependent_clauses = r"S: {<NP><VB|VBD|VBG|VBN|VBP|VBZ><NP>}"
        cp = nltk.RegexpParser(grammar=dependent_clauses)
        phrase = cp.parse(tagged_sentence)

conjunctions = re.search(r'(\w+) (and|or|as|if|so|as|but|that) (\w+)', sentence)
        prepositions = re.search(r'(\w+) (of|with|at|from|in|during|into|among) (\w+)', sentence)
```

*FIG. 3G*

```
determiners = re.search(r'(\w+) (my|a|an|no|the|one|all|its) (\w+)', sentence, particles = re.search(r'(\w+) (no|yes|of course|etc|so|as|but|that) (\w+)',
sentence)

if(conjunctions is not None):

self.phrase_structures['conjunctions'].append(conjunctions.group(0))

if (dependent_clauses is not None):

self.phrase_structures['dependent_clauses'].append(phrase)

if (prepositions is not None):

self.phrase_structures['prepositions'].append(prepositions.group(0))

if (determiners is not None):

self.phrase_structures['determiners'].append(determiners.group(0))

if (particles is not None):

self.phrase_structures['particles'].append(particles.group(0))
```

//main.py

```
from controller import TextRecognitionController import os from nested_diff import diff, patch import numpy as np import pandas as pd import tensorflow as tf import transformers from helpers import BertSemanticDataGenerator from PyDictionary import PyDictionary
```

*FIG. 3H*

```
def scanTestsDir(dir=''):
    for root, dirs, files in os.walk(dir):
        return files if __name__ == "__main__":
    filepath_dict = {'yelp':   'data/sentiment_analysis/yelp_labelled.txt',
                     'amazon': 'data/sentiment_analysis/amazon_cells_labelled.txt',
                     'imdb':   'data/sentiment_analysis/imdb_labelled.txt'} max_length = 128  # Maximum length of input sentence to the model.
    batch_size = 16
    epochs = 1
    labels = ["contradiction", "entailment", "neutral"]
    dictionary=PyDictionary()
    print (dictionary.meaning("indentation"))

files1 = scanTestsDir(dir='./tests/case1')
    print('Images: ', files1)
    TRC1 = TextRecognitionController(files1)
    rc1 = TRC1.recognize('case1')
    TRC1.get_sentences()
    TRC1.get_words()
    TRC1.get_pos_tags()
    TRC1.build_word_pos_tags_map()
    text_map1 = TRC1.get_text_map()
```

*FIG. 3I*

```
files2 = scanTestsDir(dir='./tests/case2')
print('Images: ', files2)
TRC2 = TextRecognitionController(files2)
rc2 = TRC2.recognize('case2')
TRC2.get_sentences()
TRC2.get_words()
TRC2.get_pos_tags()
TRC2.build_word_pos_tags_map()
text_map2 = TRC2.get_text_map()

print(len(diff(dict(text_map1), dict(text_map2))['U']))

sentences = [rc1, rc2]

train_df = pd.read_csv("SNLI_Corpus/snli_1.0_train.csv", nrows=50)
valid_df = pd.read_csv("SNLI_Corpus/snli_1.0_dev.csv")
test_df = pd.read_csv("SNLI_Corpus/snli_1.0_test.csv")

print(f"Total train samples : {train_df.shape[0]}")
print(f"Total validation samples: {valid_df.shape[0]}")
print(f"Total test samples: {valid_df.shape[0]}")

print(f"Sentence1: {train_df.loc[1, 'sentence1']}")
print(f"Sentence2: {train_df.loc[1, 'sentence2']}")
print(f"Similarity: {train_df.loc[1, 'similarity']}")

print("Number of missing values")
print(train_df.isnull().sum())
```

*FIG. 3J*

```
train_df.dropna(axis=0, inplace=True)

print("Train Target Distribution")
print(train_df.similarity.value_counts())

print("Validation Target Distribution")
print(valid_df.similarity.value_counts())

train_df = (
    train_df[train_df.similarity != "-"]
    .sample(frac=1.0, random_state=42)
    .reset_index(drop=True)
)
valid_df = (
    valid_df[valid_df.similarity != "-"]
    .sample(frac=1.0, random_state=42)
    .reset_index(drop=True)
)

train_df["label"] = train_df["similarity"].apply(
    lambda x: 0 if x == "contradiction" else 1 if x == "entailment" else 2
)
y_train = tf.keras.utils.to_categorical(train_df.label, num_classes=3)

valid_df["label"] = valid_df["similarity"].apply(
    lambda x: 0 if x == "contradiction" else 1 if x == "entailment" else 2
)
y_val = tf.keras.utils.to_categorical(valid_df.label, num_classes=3)
```

*FIG. 3K*

```
test_df["label"] = test_df["similarity"].apply(
    lambda x: 0 if x == "contradiction" else 1 if x == "entailment" else 2
)
y_test = tf.keras.utils.to_categorical(test_df.label, num_classes=3)

strategy = tf.distribute.MirroredStrategy()

with strategy.scope():
    # Encoded token ids from BERT tokenizer.
    input_ids = tf.keras.layers.Input(
        shape=(max_length,), dtype=tf.int32, name="input_ids"
    )
    # Attention masks indicates to the model which tokens should be attended to.
    attention_masks = tf.keras.layers.Input(
        shape=(max_length,), dtype=tf.int32, name="attention_masks"
    )
    # Token type ids are binary masks identifying different sequences in the model.
    token_type_ids = tf.keras.layers.Input(
        shape=(max_length,), dtype=tf.int32, name="token_type_ids"
    )
    # Loading pretrained BERT model.
    bert_model = transformers.TFBertModel.from_pretrained("bert-base-uncased")
    # Freeze the BERT model to reuse the pretrained features without modifying them.
    bert_model.trainable = False sequence_output, pooled_output = bert_model(
        input_ids, attention_mask=attention_masks, token_type_ids=token_type_ids
```

Add trainable layers on top of frozen layers to adapt the pretrained features on the new data.

```
bi_lstm = tf.keras.layers.Bidirectional(
    tf.keras.layers.LSTM(64, return_sequences=True)
)(sequence_output)
```

Applying hybrid pooling approach to bi_lstm sequence output.

```
avg_pool = tf.keras.layers.GlobalAveragePooling1D()(bi_lstm)
max_pool = tf.keras.layers.GlobalMaxPooling1D()(bi_lstm)
concat = tf.keras.layers.concatenate([avg_pool, max_pool])
dropout = tf.keras.layers.Dropout(0.3)(concat)
output = tf.keras.layers.Dense(3, activation="softmax")(dropout)
model = tf.keras.models.Model(
    inputs=[input_ids, attention_masks, token_type_ids], outputs=output
)

model.compile(
    optimizer=tf.keras.optimizers.Adam(),
    loss="categorical_crossentropy",
    metrics=["acc"],
)

print(f"Strategy: {strategy}")
model.summary()

train_data = BertSemanticDataGenerator(
    train_df[["sentence1", "sentence2"]].values.astype("str"),
```

*FIG. 3M*

```
    y_train,
    batch_size=batch_size,
    shuffle=True,
)
valid_data = BertSemanticDataGenerator(
    valid_df[["sentence1", "sentence2"]].values.astype("str"),
    y_val,
    batch_size=batch_size,
    shuffle=False,
)
history = model.fit(
    train_data,
    validation_data=valid_data,
    epochs=epochs,
    use_multiprocessing=True,
    workers=-1,
)

# Unfreeze the bert_model.
bert_model.trainable = True
# Recompile the model to make the change effective.
model.compile(
    optimizer=tf.keras.optimizers.Adam(1e-5),
    loss="categorical_crossentropy",
    metrics=["accuracy"],
)
model.summary()
```

*FIG. 3N*

```
history = model.fit(
    train_data,
    validation_data=valid_data,
    epochs=epochs,
    use_multiprocessing=True,
    workers=-1,
)

test_data = BertSemanticDataGenerator(
    test_df[["sentence1", "sentence2"]].values.astype("str"),
    y_test,
    batch_size=batch_size,
    shuffle=False,
)
model.evaluate(test_data, verbose=1)

def check_similarity(sentence1, sentence2):
    sentence_pairs = np.array([[str(sentence1), str(sentence2)]])
    test_data = BertSemanticDataGenerator(
        sentence_pairs, labels=None, batch_size=1, shuffle=False, include_targets=False,
    )

proba = model.predict(test_data)[0]
    idx = np.argmax(proba)
    proba = f"{proba[idx]: .2f}%"
    pred = labels[idx]
    return pred, proba
```

*FIG. 30*

```
sentence1 = "Two women are observing something together."
sentence2 = "Two women are standing with their eyes closed."
check_similarity(sentence1, sentence2)

//BertSemanticDataGenerator.py
import numpy as np
import pandas as pd
import tensorflow as tf
import transformers max_length = 128  # Maximum length of input sentence to the model.
batch_size = 16
epochs = 1
labels = ["contradiction", "entailment", "neutral"]

class BertSemanticDataGenerator(tf.keras.utils.Sequence):
    """Generates batches of data.

Args:
        sentence_pairs: Array of premise and hypothesis input sentences.
        labels: Array of labels.
        batch_size: Integer batch size.
        shuffle: boolean, whether to shuffle the data.
        include_targets: boolean, whether to incude the labels.

Returns:
        Tuples `([input_ids, attention_mask, `token_type_ids], labels)`
        (or just `[input_ids, attention_mask, `token_type_ids]`
```

*FIG. 3P*

```
    if `include_targets=False`)
"""

def __init__(
    self,
    sentence_pairs,
    labels,
    batch_size = batch_size,
    shuffle=True,
    include_targets=True,
):
    self.sentence_pairs = sentence_pairs
    self.labels = labels
    self.shuffle = shuffle
    self.batch_size = batch_size
    self.include_targets = include_targets
    # Load our BERT Tokenizer to encode the text.
    # We will use base-base-uncased pretrained model.
    self.tokenizer = transformers.BertTokenizer.from_pretrained(
        "bert-base-uncased", do_lower_case=True
    )
    self.indexes = np.arange(len(self.sentence_pairs))
    self.on_epoch_end()

def __len__(self):
    # Denotes the number of batches per epoch.
    return len(self.sentence_pairs) // self.batch_size
```

FIG. 3Q

```
def __getitem__(self, idx):
    # Retrieves the batch of index.
    indexes = self.indexes[idx * self.batch_size : (idx + 1) * self.batch_size]
    sentence_pairs = self.sentence_pairs[indexes]

# With BERT tokenizer's batch_encode_plus batch of both the sentences are
    # encoded together and separated by [SEP] token.
    encoded = self.tokenizer.batch_encode_plus(
        sentence_pairs.tolist(),
        add_special_tokens=True,
        max_length=max_length,
        return_attention_mask=True,
        return_token_type_ids=True,
        pad_to_max_length=True,
        return_tensors="tf",
        truncation=True
    )

# Convert batch of encoded features to numpy array.
    input_ids = np.array(encoded["input_ids"], dtype="int32")
    attention_masks = np.array(encoded["attention_mask"], dtype="int32")
    token_type_ids = np.array(encoded["token_type_ids"], dtype="int32")

# Set to true if data generator is used for training/validation.
    if self.include_targets:
        labels = np.array(self.labels[indexes], dtype="int32")
        return [input_ids, attention_masks, token_type_ids], labels
    else:
```

FIG. 3R

```
        return [input_ids, attention_masks, token_type_ids]

def on_epoch_end(self):
        # Shuffle indexes after each epoch if shuffle is set to True.
        if self.shuffle:
            np.random.RandomState(42).shuffle(self.indexes)
```

*FIG. 3S*

Relationship between neurons

Input layers:
1. input_ids
2. attention_masks
3. token_type_ids
4. tf_bert_model
5. bidirectional
6. global_average_pooling1d
7. global_max_pooling1d
8. concatenate
9. dropout_37
10. dense Work result of text map builder:

Hi bro! How are you? I was at the concert yesterday and you were right, it was really cool.

{'pos_tags_map': {'CC': 1, 'CD': 0, 'DT': 3, 'EX': 0, 'FW': 0, 'IN': 2, 'JJ': 2, 'JJR': 0, 'JJS': 0, 'LS': 0, 'MD': 1, 'NN': 6, 'NNS': 0, 'NNP': 2, 'NNPS': 0, 'PDT': 0, 'POS': 0, 'PRP': 7, 'PRP$': 1, 'RB': 3, 'RBR': 0, 'RBS': 0, 'RP': 0, 'TO': 1, 'UH': 0, 'VB': 1, 'VBD': 4, 'VBG': 0, 'VBN': 0, 'VBP': 2, 'VBZ': 0, 'WDT': 0, 'WP': 0, 'WP$': 0, 'WRB': 1}, 'content_words': {'nouns': ['Hi', 'bro', 'concert', 'yesterday', 'Hello', 'friend', 'concert', 'futureI|'], 'adjectives': ['cool', 'glad'], 'verbs': ['are', 'was', 'were', 'was', "'m", 'liked', 'go'], 'adverbs': ['right', 'really', 'together']}, 'phrase_structures': {'conjunctions': [], 'dependent_clauses': [Tree('S', [('Hi', 'NNP'), ('bro', 'NN'), ('!', '.')]), Tree('S', [('How', 'WRB'), ('are', 'VBP'), ('you', 'PRP'), ('?', '.')]), Tree('S', [('I', 'NN'), ('was', 'VBD'), ('at', 'IN'), ('the', 'DT'), ('concert', 'NN'), ('yesterday', 'NN'), ('and', 'CC'), ('you', 'PRP'), ('were', 'VBD'), ('right', 'RB'), (',', ','), ('it', 'PRP'), ('was', 'VBD'), ('really', 'RB'), ('cool', 'JJ'), ('.', '.')]), Tree('S', [('Hello', 'NNP'), ('my', 'PRP$'), ('friend', 'NN'), ('!', '.')]), Tree('S', [('I', 'PRP'), ("'m", 'VBP'), ('glad', 'JJ'), ('you', 'PRP'), ('liked', 'VBD'), ('it', 'PRP'), ('!', '.')]), Tree('S', [('We', 'PRP'), ('can', 'MD'), ('go', 'VB'), ('to', 'TO'), ('this', 'DT'), ('concert', 'NN'), ('together', 'RB'), ('in', 'IN'), ('the', 'DT'), ('futureI|', 'NN')])], 'prepositions': ['was at the', 'together in the'], 'determiners': ['at the concert', 'Hello my friend', 'in the futureI'], 'particles': []}, 'sentences_factors': [{'sentence_text': 'Hi bro!', 'sentence_length': 7, 'sentence_complexity': 1, 'grammar_compliance': 0, 'spelling_compliance': 0}, {'sentence_text': 'How are you?', 'sentence_length': 12, 'sentence_complexity': 2, 'grammar_compliance': 0, 'spelling_compliance': 0}, {'sentence_text': 'I was at the concert yesterday\nand you were right, it was really cool.', 'sentence_length': 70, 'sentence_complexity': 5, 'grammar_compliance': 0, 'spelling_compliance': 0}, {'sentence_text': 'Hello my friend!', 'sentence_length': 16, 'sentence_complexity': 7, 'grammar_compliance': 0, 'spelling_compliance': 0}, {'sentence_text': "I'm glad you liked it!", 'sentence_length': 22, 'sentence_complexity': 8, 'grammar_compliance': 0, 'spelling_compliance': 0}, {'sentence_text': 'We can go to\nthis concert together in the futureI|', 'sentence_length': 50, 'sentence_complexity': 11, 'grammar_compliance': 1, 'spelling_compliance': 0}], 'functional_words': {'prepositions': ['at', 'in'], 'pronouns': ['you', 'you', 'it', 'my', 'I', 'you', 'it', 'We'], 'determiners': ['the', 'this', 'the'], 'conjunctions': ['and'], 'auxiliaries': ['are', "'m"], 'particles': []}, 'text_sent_count': 0}

Hello my friend! I'm glad you liked it! We can go to this concert together in the future!

*FIG. 5A*

{'pos_tags_map': {'CC': 1, 'CD': 0, 'DT': 3, 'EX': 0, 'FW': 0, 'IN': 2, 'JJ': 2, 'JJR': 0, 'JJS': 0, 0, 'MD': 1, 'NN': 6, 'NNS': 0, 'NNP': 2, 'NNPS': 0, 'PDT': 0, 'POS': 0, 'PRP': 7, 'PRP$': 1, 'RB': 3, 'RBR': 0, 'RBS': 0, 'RP': 0, 'TO': 1, 'UH': 0, 'VB': 1, 'VBD': 4, 'VBG': 0, 'VBN': 0, 'VBP': 2, 'VBZ': 0, 'WDT': 0, 'WP': 0, 'WP$': 0, 'WRB': 1}, 'content_words': {'nouns': ['Hi', 'bro', 'concert', 'yesterday', 'Hello', 'friend', 'concert', 'future||'], 'adjectives': ['cool', 'glad'], 'verbs': ['are', 'was', 'were', 'was', "'m", 'liked', 'go'], 'adverbs': ['right', 'really', 'together']}, 'phrase_structures': {'conjunctions': [], 'dependent_clauses': [Tree('S', [('Hi', 'NNP'), ('bro', 'NN'), ('!', '.')]), Tree('S', [('How', 'WRB'), ('are', 'VBP'), ('you', 'PRP'), ('?', '.')]), Tree('S', [('|', 'NN'), ('was', 'VBD'), ('at', 'IN'), ('the', 'DT'), ('concert', 'NN'), ('yesterday', 'NN'), ('and', 'CC'), ('you', 'PRP'), ('were', 'VBD'), ('right', 'RB'), (',', ','), ('it', 'PRP'), ('was', 'VBD'), ('really', 'RB'), ('cool', 'JJ'), ('.', '.')]), Tree('S', [('Hello', 'NNP'), ('my', 'PRP$'), ('friend', 'NN'), ('!', '.')]), Tree('S', [('I', 'PRP'), ("'m", 'VBP'), ('glad', 'JJ'), ('you', 'PRP'), ('liked', 'VBD'), ('it', 'PRP'), ('!', '.')]), Tree('S', [('We', 'PRP'), ('can', 'MD'), ('go', 'VB'), ('to', 'TO'), ('this', 'DT'), ('concert', 'NN'), ('together', 'RB'), ('in', 'IN'), ('the', 'DT'), ('future||', 'NN')])], 'prepositions': ['was at the', 'together in the'], 'determiners': ['at the concert', 'Hello my friend', 'in the future|'], 'particles': []}, 'sentences_factors': [{'sentence_text': 'Hi bro!', 'sentence_length': 7, 'sentence_complexity': 1, 'grammar_compliance': 0, 'spelling_compliance': 0}, {'sentence_text': 'How are you?', 'sentence_length': 12, 'sentence_complexity': 2, 'grammar_compliance': 0, 'spelling_compliance': 0}, {'sentence_text': '| was at the concert yesterday\nand you were right, it was really cool.', 'sentence_length': 70, 'sentence_complexity': 5, 'grammar_compliance': 0, 'spelling_compliance': 0}, {'sentence_text': 'Hello my friend!', 'sentence_length': 16, 'sentence_complexity': 7, 'grammar_compliance': 0, 'spelling_compliance': 0}, {'sentence_text': "I'm glad you liked it!", 'sentence_length': 22, 'sentence_complexity': 8, 'grammar_compliance': 0, 'spelling_compliance': 0}, {'sentence_text': 'We can go to\nthis concert together in the future||', 'sentence_length': 50, 'sentence_complexity': 11, 'grammar_compliance': 1, 'spelling_compliance': 0}], 'functional_words': {'prepositions': ['at', 'in'], 'pronouns': ['you', 'you', 'it', 'my', 'I', 'you', 'it', 'We'], 'determiners': ['the', 'this', 'the'], 'conjunctions': ['and'], 'auxiliaries': ['are', "'m"], 'particles': []}, 'text_sent_count': 0}

*FIG. 5B*

Work result of Neural Network:

Model: "functional_1"

___

| Layer (type) | Output Shape | Param # | Connected to |
|---|---|---|---|

================================================================================

=========================== input_ids (InputLayer)　　　[(None, 128)]　　　0

___ attention_masks (InputLayer)　　[(None, 128)]　　　0

___ token_type_ids (InputLayer)　　[(None, 128)]　　　0

___ tf_bert_model (TFBertModel)　　((None, 128, 768), (　109482240　input_ids[0][0]
　　　　　　　　　　　　　　　　　　　　　　　　　attention_masks[0][0]
　　　　　　　　　　　　　　　　　　　　　　　　　token_type_ids[0][0]

___ bidirectional (Bidirectional)　(None, 128, 128)　　426496　　tf_bert_model[0][0]

___ global_average_pooling1d (Globa　(None, 128)　　　0　　　bidirectional[0][0]

___ global_max_pooling1d (GlobalMax　(None, 128)　　　0　　　bidirectional[0][0]

___

*FIG. 6A* concatenate (Concatenate)    (None, 256)    0    global_average_pooling1d[0][0]

global_max_pooling1d[0][0]

dropout_37 (Dropout)    (None, 256)    0    concatenate[0][0]

dense (Dense)    (None, 3)    771    dropout_37[0][0]

==================================================================================

Total params: 109,909,507

Trainable params: 109,909,507

Non-trainable params: 0

Epoch 1/2

3121/3121 [==============================] - 1574s 504ms/step - loss: 0.4698 - accuracy: 0.8181 - val_loss: 0.3787 - val_accuracy: 0.8598

Epoch 2/2

3121/3121 [==============================] - 1569s 503ms/step - loss: 0.3516 - accuracy: 0.8702 - val_loss: 0.3416 - val_accuracy: 0.8757

312/312 [==============================] - 55s 177ms/step - loss: 0.3697 - accuracy: 0.8629

[0.3696725070476532, 0.8628805875778198]

('entailment', ' 0.94%')

*FIG. 6B*

APPARATUS, SYSTEM, AND METHOD FOR ADAPTIVE PARSING AND PROCESSING OF TEXT TO FACILITATE USER ENGAGEMENT

PRIORITY

The present application claims priority to U.S. Provisional Patent Application No. 62/937,510, which was filed in the U.S. Patent and Trademark Office on Nov. 19, 2019, the entire disclosure of which is incorporated herein by reference.

INTRODUCTION

Embodiments of the present invention relate generally to an apparatus, system, and method for adaptive parsing and processing of text to facilitate user engagement. The apparatus may include one or more software applications running on an electronic device, including a smartphone, tablet, or the like.

Some users may use certain software, for example, apps on a smartphone, tablet, or other device, without due care and/or adequate engagement. For example, users of apps or other software may not be carefully reading the prompts, carefully selecting their responses, paying attention to any images or storylines that may appear on their screens, responding to prompts or questions in a timely manner, responding to such prompts or questions too quickly, responding to prompts or questions without carefully reading them, and the like.

However, it may be particularly important that users are actually engaged with a software application, especially when use of such software is recommended and/or prescribed by a medical professional and/or other clinician for the diagnosis or treatment of certain conditions such as insomnia, smoking cessation, and/or other conditions.

Moreover, adherence to treatment and guidelines is preferable to achieve successful outcomes in patients with many diseases, including, for example, Major Depressive Disorder (MDD), insomnia, lower back pain, over-active bladder, anxiety, Acute Coronary Syndrome (ACS) or any other suitable diseases. For example, after a myocardial infarction, patients who adhere to their medication regimen and lifestyle changes have better long-term outcomes compared to non-adherent patients. Despite this, adherence to evidence-based recommendations is still low. Several factors may explain low adherence: among these, the difficulties patients face in navigating their treatment, and issues with the health-care system (costs and the like).

Patient navigators are trained individuals (e.g., nurses, social workers, health workers, etc.) that help patients adhere to their treatment recommendations. Patient navigators provide personalized assistance to patients delivering education on medical conditions and factors contributing to the relevant disease, assisting with medical appointments, insurance and medications, and offering referrals to support groups or other community resources. Programs adopting patient navigators generally have better results in improving access to care.

Patient navigators have been used mostly in the management of chronic conditions such as cancer and diabetes, as well as cardiovascular disease. After a myocardial infarction, enrolling into a cardiac rehabilitation program is essential to have a successful recovery. However, only a small percentage of patients are aware of how essential it is to enroll into a cardiac rehabilitation program. After an acute cardiac event, patients who received a patient navigator intervention were 6 times more likely to know about cardiac rehabilitation and 9 times more likely to enroll into a cardiac rehabilitation program than patients who received usual care. A navigator team including different providers (nurses and pharmacists) may reduce the 30-day re-admission rate in patients with heart failure.

However, using human patient navigators may be very costly. Thus, it would be desirable to develop an apparatus, system, and method that may effectively communicate with patients regarding their condition and otherwise intervene to improve the level of care the patient receives.

It would also be desirable, to provide apparatuses, systems and methods for ensuring that users of certain software are actively engaged and interacting with a software application as directed by their medical professional and/or clinician.

BRIEF DESCRIPTION OF THE DRAWINGS

FIGS. 3A-3S show source code that can implement one or more aspects of an embodiment of the present invention;

FIGS. 5A-5B show input and processing on an electronic device that can implement one or more aspects of an embodiment of the invention; and FIGS. 6A-6B show the result of the processing on an electronic device that can implement one or more aspects of an embodiment of the invention.

While the invention is described with reference to the above drawings, the drawings are intended to be illustrative, and the invention contemplates other embodiments within the spirit of the invention.

DETAILED DESCRIPTION OF EMBODIMENTS OF THE PRESENT INVENTION

The present invention will now be described more fully hereinafter with reference to the accompanying drawings which show, by way of illustration, specific embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as devices or methods. Accordingly, the present invention may take the form of an entirely hardware embodiment, an entirely software embodiment, or an embodiment combining software and hardware aspects. The following detailed description is, therefore, not to be taken in a limiting sense.

Throughout the specification and claims, the following terms take the meanings explicitly associated herein, unless the context clearly dictates otherwise. The phrases "in one embodiment," "in an embodiment," and the like, as used herein, does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" includes plural references. The meaning of "in" includes "in" and "on."

It is noted that description herein is not intended as an extensive overview, and as such, concepts may be simplified in the interests of clarity and brevity.

All documents mentioned in this application are hereby incorporated by reference in their entirety. Any process described in this application may be performed in any order and may omit any of the steps in the process. Processes may also be combined with other processes or steps of other processes.

Figure 1:
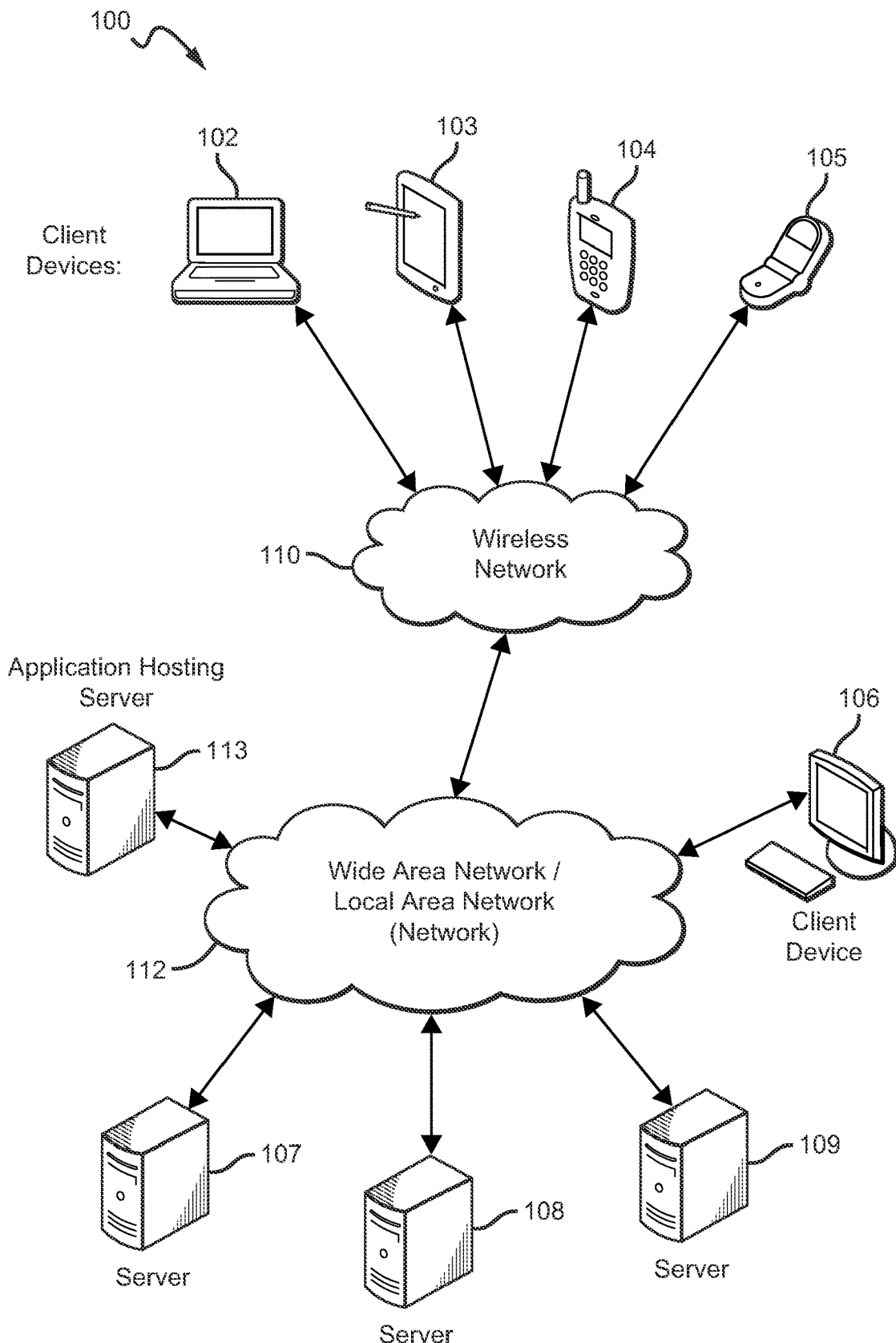
FIG. 1 illustrates a block diagram of a distributed computer system that can implement one or more aspects of an embodiment of the present invention.

FIG. 1 illustrates components of one embodiment of an environment in which the invention may be practiced. Not all of the components may be required to practice the invention, and variations in the arrangement and type of the components may be made without departing from the spirit or scope of the invention. As shown, the system 100 includes one or more Local Area Networks ("LANs")/Wide Area Networks ("WANs") 112, one or more wireless networks 110, one or more wired or wireless client devices 106, mobile or other wireless client devices 102-105, servers 107-109, and may include or communicate with one or more data stores or databases. Various of the client devices 102-106 may include, for example, desktop computers, laptop computers, set top boxes, tablets, cell phones, smart phones, smart speakers, wearable devices (such as the Apple Watch) and the like. Servers 107-109 can include, for example, one or more application servers, content servers, search servers, and the like. FIG. 1 also illustrates application hosting server 113.

Figure 2:
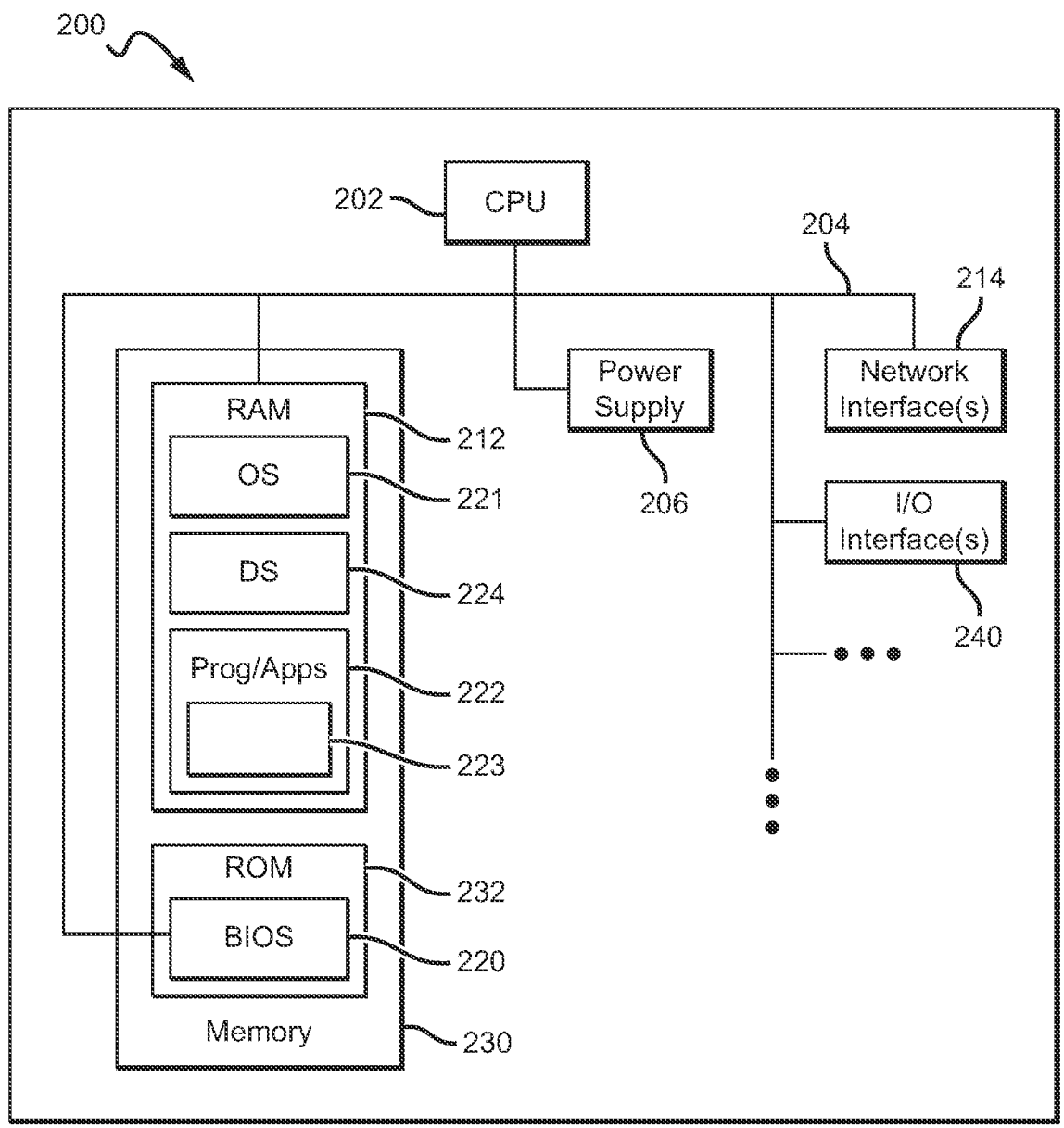
FIG. 2 illustrates a block diagram of an electronic device that can implement one or more aspects of an embodiment of the invention.

FIG. 2 illustrates a block diagram of an electronic device 200 that can implement one or more aspects of an apparatus, system and method for adaptive parsing and processing of text to facilitate user engagement (the "Engine") according to one embodiment of the invention. Instances of the electronic device 200 may include servers, e.g., servers 107-109, and client devices, e.g., client devices 102-106. In general, the electronic device 200 can include a processor/CPU 202, memory 230, a power supply 206, and input/output (I/O) components/devices 240, e.g., microphones, speakers, displays, touchscreens, keyboards, mice, keypads, microscopes, GPS components, cameras, heart rate sensors, light sensors, accelerometers, targeted biometric sensors, etc., which may be operable, for example, to provide graphical user interfaces or text user interfaces.

A user may provide input via a touchscreen of an electronic device 200. A touchscreen may determine whether a user is providing input by, for example, determining whether the user is touching the touchscreen with a part of the user's body such as his or her fingers. The electronic device 200 can also include a communications bus 204 that connects the aforementioned elements of the electronic device 200. Network interfaces 214 can include a receiver and a transmitter (or transceiver), and one or more antennas for wireless communications.

The processor 202 can include one or more of any type of processing device, e.g., a Central Processing Unit (CPU), and a Graphics Processing Unit (GPU). Also, for example, the processor can be central processing logic, or other logic, may include hardware, firmware, software, or combinations thereof, to perform one or more functions or actions, or to cause one or more functions or actions from one or more other components. Also, based on a desired application or need, central processing logic, or other logic, may include, for example, a software-controlled microprocessor, discrete logic, e.g., an Application Specific Integrated Circuit (ASIC), a programmable/programmed logic device, memory device containing instructions, etc., or combinatorial logic embodied in hardware. Furthermore, logic may also be fully embodied as software.

The memory 230, which can include Random Access Memory (RAM) 212 and Read Only Memory (ROM) 232, can be enabled by one or more of any type of memory device, e.g., a primary (directly accessible by the CPU) or secondary (indirectly accessible by the CPU) storage device (e.g., flash memory, magnetic disk, optical disk, and the like). The RAM can include an operating system 221, data storage 224, which may include one or more databases, and programs and/or applications 222, which can include, for example, software aspects of the program 223. The ROM 232 can also include Basic Input/Output System (BIOS) 220 of the electronic device.

Software aspects of the program 223 are intended to broadly include or represent all programming, applications, algorithms, models, software and other tools necessary to implement or facilitate methods and systems according to embodiments of the invention. The elements may exist on a single computer or be distributed among multiple computers, servers, devices or entities.

The power supply 206 contains one or more power components, and facilitates supply and management of power to the electronic device 200.

The input/output components, including Input/Output (I/O) interfaces 240, can include, for example, any interfaces for facilitating communication between any components of the electronic device 200, components of external devices (e.g., components of other devices of the network or system 100), and end users. For example, such components can include a network card that may be an integration of a receiver, a transmitter, a transceiver, and one or more input/output interfaces. A network card, for example, can facilitate wired or wireless communication with other devices of a network. In cases of wireless communication, an antenna can facilitate such communication. Also, some of the input/output interfaces 240 and the bus 204 can facilitate communication between components of the electronic device 200, and in an example can ease processing performed by the processor 202.

Where the electronic device 200 is a server, it can include a computing device that can be capable of sending or receiving signals, e.g., via a wired or wireless network, or may be capable of processing or storing signals, e.g., in memory as physical memory states. The server may be an application server that includes a configuration to provide one or more applications, e.g., aspects of the Engine, via a network to another device. Also, an application server may, for example, host a web site that can provide a user interface for administration of example aspects of the Engine.

Any computing device capable of sending, receiving, and processing data over a wired and/or a wireless network may act as a server, such as in facilitating aspects of implementations of the Engine. Thus, devices acting as a server may include devices such as dedicated rack-mounted servers, desktop computers, laptop computers, set top boxes, integrated devices combining one or more of the preceding devices, and the like.

Servers may vary widely in configuration and capabilities, but they generally include one or more central processing units, memory, mass data storage, a power supply, wired or wireless network interfaces, input/output interfaces, and an operating system such as Windows Server, Mac OS X, Unix, Linux, FreeBSD, and the like.

A server may include, for example, a device that is configured, or includes a configuration, to provide data or content via one or more networks to another device, such as in facilitating aspects of an example apparatus, system and method of the Engine. One or more servers may, for example, be used in hosting a Web site, such as the web site www.microsoft.com. One or more servers may host a variety of sites, such as, for example, business sites, informational sites, social networking sites, educational sites, wikis, financial sites, government sites, personal sites, and the like.

Servers may also, for example, provide a variety of services, such as Web services, third-party services, audio services, video services, email services, HTTP or HTTPS services, Instant Messaging (IM) services, Short Message Service (SMS) services, Multimedia Messaging Service (MMS) services, File Transfer Protocol (FTP) services, Voice Over IP (VOIP) services, calendaring services, phone services, and the like, all of which may work in conjunction with example aspects of an example systems and methods for the apparatus, system and method embodying the Engine. Content may include, for example, text, images, audio, video, and the like.

In example aspects of the apparatus, system and method embodying the Engine, client devices may include, for example, any computing device capable of sending and receiving data over a wired and/or a wireless network. Such client devices may include desktop computers as well as portable devices such as cellular telephones, smart phones, display pagers, Radio Frequency (RF) devices, Infrared (IR) devices, Personal Digital Assistants (PDAs), handheld computers, GPS-enabled devices tablet computers, sensor-equipped devices, laptop computers, set top boxes, wearable computers such as the Apple Watch and Fitbit, integrated devices combining one or more of the preceding devices, and the like.

Client devices such as client devices 102-106, as may be used in an example apparatus, system and method embodying the Engine, may range widely in terms of capabilities and features. For example, a cell phone, smart phone or tablet may have a numeric keypad and a few lines of monochrome Liquid-Crystal Display (LCD) display on which only text may be displayed. In another example, a Web-enabled client device may have a physical or virtual keyboard, data storage (such as flash memory or SD cards), accelerometers, gyroscopes, respiration sensors, body movement sensors, proximity sensors, motion sensors, ambient light sensors, moisture sensors, temperature sensors, compass, barometer, fingerprint sensor, face identification sensor using the camera, pulse sensors, heart rate variability (HRV) sensors, beats per minute (BPM) heart rate sensors, microphones (sound sensors), speakers, GPS or other location-aware capability, and a 2D or 3D touch-sensitive color screen on which both text and graphics may be displayed. In some embodiments multiple client devices may be used to collect a combination of data. For example, a smart phone may be used to collect movement data via an accelerometer and/or gyroscope and a smart watch (such as the Apple Watch) may be used to collect heart rate data. The multiple client devices (such as a smart phone and a smart watch) may be communicatively coupled.

Client devices, such as client devices 102-106, for example, as may be used in an example apparatus, system and method implementing the Engine, may run a variety of operating systems, including personal computer operating systems such as Windows, iOS or Linux, and mobile operating systems such as iOS, Android, Windows Mobile, and the like. Client devices may be used to run one or more applications that are configured to send or receive data from another computing device. Client applications may provide and receive textual content, multimedia information, and the like. Client applications may perform actions such as browsing webpages, using a web search engine, interacting with various apps stored on a smart phone, sending and receiving messages via email, SMS, or MMS, playing games (such as fantasy sports leagues), receiving advertising, watching locally stored or streamed video, or participating in social networks.

In example aspects of the apparatus, system and method implementing the Engine, one or more networks, such as networks 110 or 112, for example, may couple servers and client devices with other computing devices, including through wireless network to client devices. A network may be enabled to employ any form of computer readable media for communicating information from one electronic device to another. The computer readable media may be non-transitory. A network may include the Internet in addition to Local Area Networks (LANs), Wide Area Networks (WANs), direct connections, such as through a Universal Serial Bus (USB) port, other forms of computer-readable media (computer-readable memories), or any combination thereof. On an interconnected set of LANs, including those based on differing architectures and protocols, a router acts as a link between LANs, enabling data to be sent from one to another.

Communication links within LANs may include twisted wire pair or coaxial cable, while communication links between networks may utilize analog telephone lines, cable lines, optical lines, full or fractional dedicated digital lines including T1, T2, T3, and T4, Integrated Services Digital Networks (ISDNs), Digital Subscriber Lines (DSLs), wireless links including satellite links, optic fiber links, or other communications links known to those skilled in the art. Furthermore, remote computers and other related electronic devices could be remotely connected to either LANs or WANs via a modem and a telephone link.

A wireless network, such as wireless network 110, as in an example apparatus, system and method implementing the Engine, may couple devices with a network. A wireless network may employ stand-alone ad-hoc networks, mesh networks, Wireless LAN (WLAN) networks, cellular networks, and the like.

A wireless network may further include an autonomous system of terminals, gateways, routers, or the like connected by wireless radio links, or the like. These connectors may be configured to move freely and randomly and organize themselves arbitrarily, such that the topology of wireless network may change rapidly. A wireless network may further employ a plurality of access technologies including 2nd (2G), 3rd (3G), 4th (4G) generation, Long Term Evolution (LTE) radio access for cellular systems, WLAN, Wireless Router (WR) mesh, and the like. Access technologies such as 2G, 2.5G, 3G, 4G, and future access networks may enable wide area coverage for client devices, such as client devices with various degrees of mobility. For example, a wireless network may enable a radio connection through a radio network access technology such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, and the like. A wireless network may include virtually any wireless communication mechanism by which information may travel between client devices and another computing device, network, and the like.

Internet Protocol (IP) may be used for transmitting data communication packets over a network of participating digital communication networks, and may include protocols such as TCP/IP, UDP, DECnet, NetBEUI, IPX, Appletalk, and the like. Versions of the Internet Protocol include IPv4 and IPv6. The Internet includes local area networks (LANs), Wide Area Networks (WANs), wireless networks, and long-haul public networks that may allow packets to be communicated between the local area networks. The packets may be transmitted between nodes in the network to sites each of which has a unique local network address. A data communication packet may be sent through the Internet from a user site via an access node connected to the Internet. The packet may be forwarded through the network nodes to any target site connected to the network provided that the site address of the target site is included in a header of the packet. Each packet communicated over the Internet may be routed via a path determined by gateways and servers that switch the packet according to the target address and the availability of a network path to connect to the target site.

The header of the packet may include, for example, the source port (16 bits), destination port (16 bits), sequence number (32 bits), acknowledgement number (32 bits), data offset (4 bits), reserved (6 bits), checksum (16 bits), urgent pointer (16 bits), options (variable number of bits in multiple of 8 bits in length), padding (may be composed of all zeros and includes a number of bits such that the header ends on a 32 bit boundary). The number of bits for each of the above may also be higher or lower.

A "content delivery network" or "content distribution network" (CDN), as may be used in an example apparatus, system and method implementing the Engine, generally refers to a distributed computer system that comprises a collection of autonomous computers linked by a network or networks, together with the software, systems, protocols and techniques designed to facilitate various services, such as the storage, caching, or transmission of content, streaming media and applications on behalf of content providers. Such services may make use of ancillary technologies including, but not limited to, "cloud computing," distributed storage, DNS request handling, provisioning, data monitoring and reporting, content targeting, personalization, and business intelligence. A CDN may also enable an entity to operate and/or manage a third party's web site infrastructure, in whole or in part, on the third party's behalf.

A Peer-to-Peer (or P2P) computer network relies primarily on the computing power and bandwidth of the participants in the network rather than concentrating it in a given set of dedicated servers. P2P networks are typically used for connecting nodes via largely ad hoc connections. A pure peer-to-peer network does not have a notion of clients or servers, but only equal peer nodes that simultaneously function as both "clients" and "servers" to the other nodes on the network.

Embodiments of the present invention include apparatuses, systems, and methods implementing the Engine. Embodiments of the present invention may be implemented on one or more of client devices 102-106, which are communicatively coupled to servers including servers 107-109. Moreover, client devices 102-106 may be communicatively (wirelessly or wired) coupled to one another. In particular, software aspects of the Engine may be implemented in the program 223. The program 223 may be implemented on one or more client devices 102-106, one or more servers 107-109, and 113, or a combination of one or more client devices 102-106, and one or more servers 107-109 and 113.

As noted above, embodiments of the present invention, which may be implemented at least in part in the program 223, relate to apparatuses, methods and systems for adaptive parsing and processing of text to facilitate user engagement. The adaptive parsing and processing of text may include the use of a neural network and, more specifically, a convolutional neural network.

An embodiment of the present invention, which may be implemented at least in part in the program 223, includes software that functions as a digital patient navigator (DPN). That is, the DPN is a personal assistant running on an electronic device of a user, the goal of which is to facilitate a user's engagement in completing certain tasks set by the DPN (i.e., "missions") and thus promote behavior change.

The behavior change may, for example, include smoking cessation. The DPN may include features that: (1) establish a relationship between the software and the user; and (2) adjust content delivery based on a user's needs (for example, users who are smokers and do not strongly adhere to treatment regimens such as medications, psychological interventions, or any other suitable treatment protocol will receive all the missions for these two Mechanisms of Action (MOAs) and fewer missions for other MOAs, which the DPN determines as not relevant (or less relevant) from an initial survey conducted by the DPN). The DPN will attempt to maintain adherence to a particular treatment by interacting with the DPN in a real-life setting.

As noted above, one feature of the DPN is establishing a relationship with the user interacting with the DPN. Establishing a relationship includes a matching and mirroring feature, as discussed in further detail below.

In real-life, establishing a relationship is a key component to engage people in behavior change, one of the purposes of the DPN. This is true for psychotherapy as much as for patient navigators and any other provider.

The DPN will emulate the matching and mirroring component of real-life social interaction such that the messages directed to the user will be highly personalized and similar in language and statement construction style to the one used by the user, who, in turn, will have the feeling of interacting with "someone" who is similar to the user and can understand and sympathize with the user.

Moreover, to increase adherence to the program the user is being asked to follow, other real-life features such as shared decision-making and prioritizing based on current needs may be used.

Establishing a relationship is essential to engage patients in behavioral interventions. In "real-life" settings, this may be accomplished by adopting patient navigators who are culturally competent. Indeed, a patient navigator who belongs to the same culture and background of the patient promotes the perception of speaking the "same language" and, thus, sharing content with someone who can understand.

To emulate this key aspect of a real-life patient navigator, the DPN will interact with the user through specific sentence structures developed using techniques of matching and mirroring.

Matching and mirroring are techniques used in Neuro-Linguistic Programming to inform a goal-oriented interpersonal communication style. In social interactions, people tend to automatically synchronize their communication styles to enhance mutual attraction and optimize understanding. Matching and Mirroring techniques refer to the copying and reflecting of aspects of the other person's communication style (verbal, facial expression, posture, and the like). For example, if a patient navigator is conversing with a patient, in order to synchronize communication styles, it would be beneficial for the patient navigator to use similar vocabulary and sentence structure to the patient.

The DPN will be developed by using an extracting and analyzing function that extracts (e.g., parses) and analyzes content words as well as other characteristics utilized by the user to structure sentences when sending messages or speaking with the user.

After extraction, the DPN will use these characteristics to personalize text messages and prompts sent to the user with the goal of giving the user the feeling of being in contact with "someone" who is similar to the user.

More specifically, implementing the matching and mirroring software functionality will include the following. The DPN will leverage text mining (e.g., parsing) techniques to extract characteristics of a user's statements. The DPN will include an extracting and analyzing function that will extract and analyze content words as well as other characteristics utilized by the user to structure sentences when sending communications (whether text or voice) to the user.

The DPN will categorize words used by the user in communicating with the DPN. Moreover, the DPN, after obtaining a user's permission, may scan a user's electronic device (such as a smartphone) and parse all text on the phone created by the user such as emails, text messages, social media posts, What's App messages, attachments sent by the user such as Microsoft Word Documents, and the like in order to expedite the matching and mirroring software functionality. That is, depending on the amount of communication from the user to the DPN, it may take some time to obtain an adequate sample of the words and/or sentence structures a user uses. However, by analyzing text previously (or any newly created text, analyzed in real-time) created by the user, the DPN may almost immediately run its matching and mirror software functionality and determine the words and sentence structure it should use when communicating with the user.

In another embodiment, the DPN may access sound files created by the user to determine how to properly match and mirror. For example, the DPN may access What's App voice messages previously sent by the user to other users, use speech recognition to convert words spoken in the voice message into text to be analyzed, and then used in the matching and mirroring process.

In another embodiment, the DPN may use the microphone functionality of the electronic device (e.g., smartphone) of the user and use speech recognition to convert words spoken by the user into text to be analyzed and then used in the matching and mirroring process. For example, the user may be speaking to another person within a close enough distance of the electronic device for the microphone to capture such speech (even if the user is not actively using the electronic device), the DPN may then convert the speech to text to be analyzed and then used in the matching and mirroring process.

In another embodiment, the DPN may, in real-time, analyze the user communicating using the electronic device. For example, the DPN may use speech recognition to convert words spoken by the user (for example, during a phone call or video chat using the electronic device) into text to be analyzed and then used in the matching and mirroring process.

For all of the above, the speech recognition may take place on the electronic device used by the user or the voice data may be transmitted to another device communicatively coupled to the electronic device (e.g., a server). The other device may then use speech recognition to convert the speech into text and/or analyze the text for the matching and mirroring process. The matching and mirroring functionality may also take place on the other device.

In another embodiment, the DPN may access, process, match and mirror another person's text (not the user). That is, users are more likely to speak with other people who speak in a similar manner to them. Thus, the DPN may access a voice message left for the user by another user and, depending on the frequency of communications between the user and the other person, may assume that the two styles of communication (the other user's and the user's) are similar.

Once the relevant text is obtained, the matching and mirroring process runs. The DPN will include an extracting and analyzing (parsing) function and will extract and analyze content words as well as other characteristics utilized by the user to structure sentences. The various portions of the communications analyzed by the DPN are as follows.

Function words—Function words mostly express a grammatical relationship between other words and have little lexical meaning on their own. They essentially function as "grammatical glue." For this reason, function words are produced mostly automatically (not consciously) during the structuring of a sentence. As a result, they can be used as markers of individual differences.

Function words include:
Prepositions (i.e., of, at, in, without, between);
Pronouns (i.e., he, they, anybody, it, one);
Determiners (i.e., the, a, that, my, more, much, either, neither);
Conjunctions (i.e., and, that, when, while, although);
Auxiliary (i.e., verbs be (is, am, are), have, got, do); and
Particles (i.e., no, not, nor, as)

Content words—Content words are words that have meaning and are used to provide the most important information when producing language.

Content words include:
Nouns (i.e., John, room, answer);
Adjectives (i.e., happy, new, large, grey);
"Full" verbs (i.e., search, grow, hold, have); and
Adverbs (i.e., really, completely, very, also, enough).

Content words are used to extract information on a user's culture, background, language, level of education, place of birth, nationality, current geographical location, and the like, to culturally tailor the DPN messages to the user. For example, if a user regularly uses the term "y'all" or its phonetic equivalents, it may be determined that user's geographical location is in one of the southern states of the United States of America. Moreover, if a user regularly uses Spanish, it may be determined that the user was either born in a country where Spanish is regularly spoken or is currently in a country where Spanish is regularly spoken.

Additional aspects of the matching and mirroring process is as follows:
- Determine how each sentence opens (repetition of the same word, pronoun, subject);
- Determine length of each sentence (short vs. long); and
- Identify sentence type as follows:
  - Simple sentences: A simple sentence is an independent clause with no conjunction or dependent clause.
  - Compound sentences: A compound sentence is two independent clauses joined by a conjunction (e.g., and, but, or, for, nor, yet, so).
  - Complex sentences: A complex sentence contains one independent clause and at least one dependent clause. The clauses in a complex sentence are combined with conjunctions and subordinators, terms that help the dependent clauses relate to the independent clause. Subordinators can refer to the subject (who, which), the sequence/time (since, while), or the causal elements (because, if) of the independent clause.
  - Compound-complex sentences: A compound-complex sentence contains multiple independent clauses and at least one dependent clause. These sentences will contain both conjunctions and subordinators.

The above characteristics may be assessed using the existing data on the user's electronic device (emails, What's App voice messages, and the like).

In the alternative, the above characteristics may be assessed using a predetermined number of open-ended questions in the initial survey conducted by the DPN. That is, the DPN may ask the user multiple open-ended questions and analyze the user's responses. For example, the DPN may ask a question such as, "In your own words, please describe your relationship with your parents." The user would then submit an open-ended response of one or more sentences, which would then be analyzed by the DPN.

After the above analysis is complete, in communicating with the user, when creating the text message (or voice message) to be sent to the user by the DPN, the text messages will be informed using function words and sentence structure as similar as possible to those used by the user. With respect to content words, however, the DPN will generate text messages that will use only a predetermined number (such as, for example, 10%, 20%, 30%, 40%, 50%, 60%, 70%, 80%, or 90%) of the words used by the user. The remaining proportion of words will include synonyms (the closest in lexical terms to the original word). This will be done so as not to give the user the feeling of being imitated and mocked.

Once the DPN determines how best to communicate with the user (e.g., what words and sentence structure to use when communicating with the user), the DPN will prioritize MOAs and deliver missions based on user's needs, as discussed in more detail below. That is, DPN will interact with the user to deliver missions for the purpose of correcting certain user behaviors (such as smoking).

Mission 1: Shared Decision-Making to Prioritize MOAs Delivery.

While all users may receive the same number of missions, the number of missions for each MOA will be adjusted based on the user's needs evaluated in an initial survey, and the user's feedback.

The initial survey will contain a series of questions aimed at evaluating a user's needs. It will include questions on past and present adherence to medical recommendations, nutrition and the need for weight loss, smoking status, physical activity and medical recommendations for physical activity post myocardial infarction, stress and depression, as well as social support and isolation. The DPN will select more important MOAs, the number of missions per MOA based on a user's answers, and a user's feedback.

For example, based on the initial survey, user 1 reports low adherence, cigarette smoking, need for weight loss, but no stress or depression. The DPN would summarize these results and ask for feedback (e.g., "Hey (insert user's name), based on your answers, it seems that the areas where I could help you the most are quitting smoking, taking your medications and eating better. Is this correct?"

If the user responds YES, the DPN asks the user to sign a behavioral contract (see mission below) and prioritize MOAs and missions accordingly. For example, the DPN may provide the user: all missions (or a predetermined number) for adherence, all missions (or a predetermined number) for smoking (if low motivation to quit, add motivational interviewing for smoking), all missions (or a predetermined number) for diet, and 1 or 2 missions for risk factor optimization.

If the user responds NO, the DPN asks what areas among our MOAs the user would like help with and then conduct a motivational interview for areas of needs that user is not ready to change yet (e.g., if user is a smoker but does not want help to quit, conduct motivational interview for smoking cessation).

Mission 2. Behavioral Contract to Complete all Missions.

Behavioral contracts are written agreements that patients make with themselves, healthcare providers, or researchers, in which they commit to engage in a set of behaviors aimed at reaching a final goal, which is generally to change one or more habits such as smoking. Ultimately, behavioral contracts aim to improve the patients' engagement in behavior change.

The DPN will briefly introduce to the user the behavioral contract and its goal. For example: "A behavioral contract is a written agreement with yourself, the goal of which is to motivate you to engage in the changes you need to make in order to be healthier and live longer. The idea is that once you write down your commitment, you'll be more motivated to carry out the actions needed to achieve your health goals." The quoted text is first revised based on the matching and mirroring features, discussed above.

The DPN will ensure that the user understands that the aim of the contract is exclusively to facilitate their commitment to the behavior change(s) of their choice and not a legally binding contract. This is so as not to compromise the shared decision-making process and "alliance" between the DPN and the user.

The DPN will then ask the user if he/she wants to sign a behavioral contract to commit to complete all missions that will be delivered on the specific areas of need emerged in mission 1.

If the user responds YES: The DPN will present the following contract to sign on the user's electronic device:

"Based on my understanding of my health status and awareness of the medical recommendations, I have decided to commit to complete all the missions of this program with the goal of acquiring healthier habits and improve my cardiovascular health. I understand that completing this program is in my best interest and I agree to actively engage in the actions required to accomplish this goal." The DPN will then ask the user to date and sign electronically.

If the user responds NO: The DPN may state as follows to the user: "Okay, we understand that change your habits is difficult. Why don't we start so that you can familiarize with the missions and then get back to the behavioral contract in a couple of weeks to see if you have changed your mind?"

As mentioned, any of the above quotes may be revised based on the matching and mirroring features, discussed above.

Mission 3. Weekly Check-Ins and Mission Re-Adjustment.

The DPN will be conduct weekly check-ins with the user and determine whether it is necessary to re-adjust any of the missions.

A user's needs may not be stable over the course of the program (which may be an 8 week program). A user may start with low adherence and quickly improve with the help of, for example, medication reminders. As a result, the user may no longer need the delivery of all missions for adherence but may benefit from an increase in the number of missions for other MOAs.

To further tailor the program to the needs of the user, the DPN will conduct weekly check-ins, during which it will assess the occurrence (or non-occurrence) of changes in a user's needs through a shortened version of the initial survey (e.g., for adherence, the DPN will ask if the user has been taking their medications every day and if they have scheduled their follow up visits, stress and depression will be assessed through emoticons and yes-or-no answers). The results will be compared to their previous assessment and the delivery of the missions will be adjusted accordingly.

For example, for week 1, the DPN would rely on the baseline survey and provide the users with the missions determined following the baseline (initial) survey. However, if after the week 4 weekly check-in, a user reports increased stress, the DPN may, for week 5, increase the number of missions related to stress from 2 to 3. Additionally, to keep the number of total missions in a week constant, the DPN may decrease the number of missions on MOAs where the weekly check-in indicates an improvement.

FIGS. 3A-3S show source code that can implement one or more aspects of an embodiment of the present invention. FIGS. 3A-3S include the following four algorithms:

First Algorithm (the "Data Capture Program").
 a. Captures text messages and emails from a user's smartphone.
 b. Saves or cuts the text messages and emails into text snippets, maintaining the sequential relationship between snippets.

Second Algorithm (the "Categorization Program")
 a. Receives data from the Data Capture Program.
 b. Evaluates each the snippet according to the following word and phrase categories:
  i. Functional Words:
   1. Prepositions (e.g., of, with, at, from, in, during, including, into, upon, until, without, between, towards, against, among, throughout, despite, concerning, etc.);
   2. Pronouns (e.g., he, they, anybody, it one);
   3. Determiners (e.g., my, a, an, no, the, one, all, its, our, any two, his, few, her, what, this, that, your, more, some, many, most, such, very, each, much, both, less, next, half, these, their, which, three, first, those, every, least, quite, whose, fewer, another, several, either, neither, etc.);
   4. Conjunctions (e.g., or, as, if, so, and, for, but, how, why, now, yet, nor, that, when, like, only, once, plus, while, since, before, though, either, unless, except, because, without, whether, whereas, neither although, whenever, etc.);
   5. Auxiliaries (e.g., am, is, are, was, were, being, been, be, have, has, had, do, does, did, will, would, shall, should, may, might, must, can, could, etc.); and
   6. Particles (e.g., to _____, preposition_verb, interjections, no, yes, etc.).
  ii. Content Words
   1. Nouns (e.g., John, room, answer);
   2. Adjectives (e.g., happy, new, large, grey);
   3. Verbs (e.g., search, grow, hold, have); and
   4. Adverbs (e.g., really, completely, very, also, enough).
  iii. Phrase Structures
   1. Conjunctions (phrases that contain conjunction words)
   2. Dependent Clauses (noun+verb)
   3. Prepositions (phrases that contain preposition words)
   4. Determiners (phrases that contain determiners)
   5. Particles (phrases that contain particles)
 c. Tags each snippet with information relating to the following "sentence factors":
  i. Sentence Length
   1. Calculates the number of words in each sentence.
  ii. Sentence Complexity
   1. Calculates the number of phrase structures within a sentence.
  iii. Grammar Compliance
   1. Engage with API of a generic grammar check tool.
  iv. Spelling Compliance
   1. Engage with API of a generic spelling check tool.
  v. Vocabulary Level
   1. Calculate Vocabulary Level by assigning numerical values to words in snippets based on vocabulary frequency tables, with less frequently used words scoring higher values.
 d. Identify snippet content
  i. Search, for example, Simple English Wikipedia, entries for the content words used in snippets and sequential snippets to determine snippet content.
  ii. Cross-link the snippets to the Wikipedia entries that most closely match.

Third Algorithm (the "Friendship Intensity Program"):
 a. Identifies the two closest friends with whom the user communicates based on data received from the Data Capture Program, such as the amount, frequency, and historical duration/length of text communication exchanged.

Fourth Algorithm (the "Communication Style and Personality Imitation AI Training Program"):
 a. Training program for a Neural Network.
 b. Receives data from the Categorization Program, which is used to train the AI.
 c. This program should train separate neural networks for the primary user (the "AI Mirror Personality") and as well as each of the two friends identified by the Friendship Intensity Program (the "AI Friend Personalities").
 d. Each neural network is then be capable of initiating and responding to communications with the primary user via an existing messaging platform.

Figure 4:
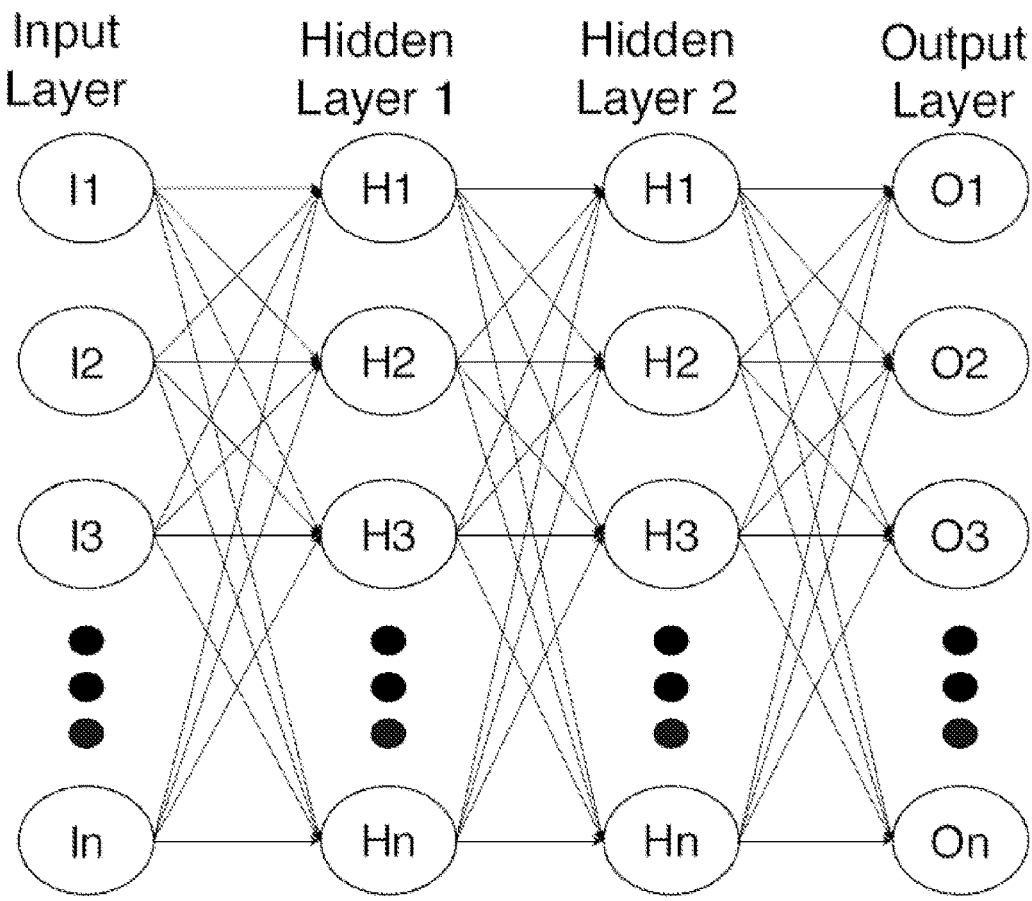
FIG. 4 is a diagram showing multiple layers of a neural network algorithm according to an embodiment of the present invention.

FIG. 4 is a diagram showing multiple layers of a neural network algorithm according to an embodiment of the present invention (which may implement the source code shown in FIGS. 3A-3S).

FIG. 5A-5B show the capturing functionality (i.e., the Data Capture Program) for text messages and emails from a user's smartphone. The software returns captured text, saves the text messages and emails into text snippets, and transmits the data to the Categorization Program. The Categorization Program then receives data from the Data Capture Program and builds a map of evaluated snippets.

The output for the text of the first user shows input received from an electronic device of the user ("Hi bro! How are you? I was at the concert yesterday and you were right, it was really cool.") as well as the input. FIG. 5B shows output of text from a second user. FIGS. 6A-6B shows the result of the algorithm performed by a neural network. The software analyzes the communication style and personality of the user. The data from the Categorization Program is used to train the AI application (neural network). The process can take, for example, up to 10 hours depending on the performance of the neural network server, the platform the server is placed on, and on the data volume. The separate neural networks are trained for the friends identified by the AI Friend Personalities program. There is a pool of parameters and layers which function similar to neurons and save appropriate data. For the case shown in FIGS. 6A-6B, the trainable parameters count is 109,909,507. The text for responding to the user is returned from the algorithm. The communication with the messaging platform may be implemented in Python Jabber module: python-XMPP.

While this invention has been described in conjunction with the embodiments outlined above, many alternatives, modifications and variations will be apparent to those skilled in the art upon reading the foregoing disclosure. Accordingly, the embodiments of the invention, as set forth above, are intended to be illustrative, not limiting. Various changes may be made without departing from the spirit and scope of the invention.

What is claimed is:

1. A computer implemented method for adaptive parsing and processing of text to facilitate user engagement in a remote computing environment, the method comprising:
   receiving data comprising one or more snippets;
   tagging the one or more snippets according to one or more categories including at least function word categories or content word categories;
   training a neural network based on at least one of the one or more categories and the one or more snippets;
   receiving an input content from an electronic device of a user, wherein the input content is received in response to one or more open-ended questions, the input content comprising a plurality of words, the plurality of words comprising one or more content words and one or more function words;
   following the receiving of the input content, extracting the one or more function words and the one or more content words from the input content;
   determining, via the neural network, based on extraction of the input content including the one or more function words and the one or more content words, user information;
   determining, based on the user information, output content to output to the user; and
   outputting, to a screen of the electronic device of the user, the output content.

2. The adaptive parsing and processing method according to claim 1, wherein the user information comprises at least one of communication style and personality of the user.

3. The adaptive parsing and processing method according to claim 1, wherein the user information comprises at least one of: the user's culture, the user's grammar level, the user's spelling level, the user's level of education, the user's nationality, the user's primary language, the user's geographical location, or the user's place of birth.

4. The adaptive parsing and processing method according to claim 1, wherein extracting the function words comprises determining whether a word of the input content is at least one of a preposition, pronoun, determiner, conjunction, auxiliary, or particle.

5. The adaptive parsing and processing method according to claim 1, wherein extracting the content words comprises determining whether a word of the input content is at least one of a noun, an adjective, a full verb, or an adverb.

6. The adaptive parsing and processing method according to claim 1, wherein determining the output content to output to the user comprises determining an opening of a first sentence.

7. The adaptive parsing and processing method according to claim 1, wherein determining the output content to output to the user comprises determining a length of a first sentence.

8. The adaptive parsing and processing method according to claim 1, wherein determining the output content to output to the user comprises determining a complexity of a first sentence.

9. The adaptive parsing and processing method according to claim 1, wherein determining the output content to output to the user comprises determining a sentence type of a first sentence, wherein the sentence type comprises at least one of a simple sentence, a compound sentence, a complex sentence, or a compound-complex sentence.

\* \* \* \* \*